United States Patent
Chappa et al.

(10) Patent No.: US 10,124,088 B2
(45) Date of Patent: Nov. 13, 2018

(54) LUBRICIOUS MEDICAL DEVICE ELEMENTS

(71) Applicant: SurModics, Inc., Eden Prairie, MN (US)

(72) Inventors: Ralph A. Chappa, Ham Lake, MN (US); Nathan A. Lockwood, Minneapolis, MN (US); Joseph Schmidt McGonigle, Minneapolis, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 14/860,128

(22) Filed: Sep. 21, 2015

(65) Prior Publication Data
US 2016/0089480 A1    Mar. 31, 2016

Related U.S. Application Data

(60) Provisional application No. 62/057,063, filed on Sep. 29, 2014.

(51) Int. Cl.
*A61L 29/14* (2006.01)
*A61L 29/08* (2006.01)
(Continued)

(52) U.S. Cl.
CPC ............ *A61L 29/14* (2013.01); *A61L 29/049* (2013.01); *A61L 29/085* (2013.01);
(Continued)

(58) Field of Classification Search
CPC ....... A61L 31/041; A61L 29/14; A61L 29/049
(Continued)

(56) References Cited

U.S. PATENT DOCUMENTS

| 4,195,637 A | 4/1980 | Gruntzig et al. |
| 4,973,493 A | 11/1990 | Guire |

(Continued)

FOREIGN PATENT DOCUMENTS

| CN | 104185661 | 12/2014 |
| CR | 2014-0349 | 11/2014 |

(Continued)

OTHER PUBLICATIONS

"International Search Report & Written Opinion," for PCT/US2015/052565 dated Dec. 9, 2015 (14 pages).
(Continued)

*Primary Examiner* — Michael M Dollinger
(74) *Attorney, Agent, or Firm* — Pauly, DeVries Smith & Deffner LLC

(57) ABSTRACT

Embodiments of the invention include medical device elements formed from polymers with lubricious properties. In an embodiment, a method of forming a medical device element is included. The method can include mixing a first polymeric component and a second polymeric component to form a polymer mixture. The method can further include forming the polymer mixture into the medical device element. The method can also include treating the polymer mixture with at least one of an acid or a base. In an embodiment, a medical device is included. The medical device can include a lubricious element, the lubricious element comprising a mixture of a first polymeric component and a second polymeric component. The second polymeric component can include a polymer that is treated with at least one of an acid or a base after formation of the element. Other embodiments are also included herein.

8 Claims, 1 Drawing Sheet

(51) Int. Cl.
  *A61L 29/04* (2006.01)
  *C08J 3/20* (2006.01)
  *A61L 31/04* (2006.01)
  *A61L 31/10* (2006.01)
  *A61L 31/14* (2006.01)

(52) U.S. Cl.
  CPC ............. *A61L 31/041* (2013.01); *A61L 31/10* (2013.01); *A61L 31/14* (2013.01); *C08J 3/203* (2013.01); *A61L 2400/10* (2013.01); *A61L 2420/06* (2013.01); *C08J 2375/04* (2013.01); *C08J 2429/10* (2013.01); *C08J 2437/00* (2013.01)

(58) Field of Classification Search
  USPC ....................................................... 525/127
  See application file for complete search history.

(56) References Cited

U.S. PATENT DOCUMENTS

| | | |
|---|---|---|
| 4,979,959 A | 12/1990 | Guire |
| 4,990,357 A | 2/1991 | Karakelle et al. |
| 5,001,009 A * | 3/1991 | Whitbourne ............ A61L 27/34 428/412 |
| 5,002,582 A | 3/1991 | Guire et al. |
| 5,039,485 A | 8/1991 | Conviser et al. |
| 5,041,089 A | 8/1991 | Mueller et al. |
| 5,087,246 A | 2/1992 | Smith |
| 5,263,992 A | 11/1993 | Guire |
| 5,318,587 A | 6/1994 | Davey |
| 5,382,234 A | 1/1995 | Cornelius et al. |
| 5,414,075 A | 5/1995 | Swan et al. |
| 5,512,329 A | 4/1996 | Guire et al. |
| 5,554,120 A * | 9/1996 | Chen ..................... A61L 29/049 525/166 |
| 5,571,089 A | 11/1996 | Crocker |
| 5,637,460 A | 6/1997 | Swan et al. |
| 5,662,960 A * | 9/1997 | Hostettler ............ A61L 29/085 427/2.28 |
| 5,670,558 A | 9/1997 | Onishi et al. |
| 5,714,360 A | 2/1998 | Swan et al. |
| 5,731,087 A * | 3/1998 | Fan ....................... A61L 29/085 428/412 |
| 5,776,101 A | 7/1998 | Goy |
| 5,807,331 A | 9/1998 | Den Heijer et al. |
| 5,858,653 A | 1/1999 | Duran et al. |
| 5,882,336 A | 3/1999 | Janacek |
| 5,891,109 A | 4/1999 | Inoue et al. |
| 6,066,118 A | 5/2000 | Inoue et al. |
| 6,077,698 A | 6/2000 | Swan et al. |
| 6,156,345 A | 12/2000 | Chudzik et al. |
| 6,176,849 B1 * | 1/2001 | Yang ..................... A61L 29/085 604/172 |
| 6,278,018 B1 | 8/2001 | Swan |
| 6,394,995 B1 | 5/2002 | Solar et al. |
| 6,517,515 B1 | 2/2003 | Eidenschink |
| 6,603,040 B1 | 8/2003 | Swan |
| 6,623,504 B2 | 9/2003 | Vrba et al. |
| 6,896,842 B1 | 5/2005 | Hamilton et al. |
| 6,924,390 B2 | 8/2005 | Swan |
| 7,056,533 B2 | 6/2006 | Chudzik et al. |
| 7,138,541 B2 | 11/2006 | Swan |
| 7,163,523 B2 | 1/2007 | Devens, Jr. et al. |
| 7,192,484 B2 | 3/2007 | Chappa et al. |
| 7,348,055 B2 | 3/2008 | Chappa et al. |
| 7,550,444 B2 * | 6/2009 | Stucke ..................... A61L 27/34 424/423 |
| 7,691,476 B2 | 4/2010 | Finley et al. |
| 7,772,393 B2 | 8/2010 | Guire et al. |
| 8,889,760 B2 | 11/2014 | Kurdyumov et al. |
| 8,927,000 B2 * | 1/2015 | Chappa .................. A61L 29/044 424/422 |
| 9,340,876 B2 | 5/2016 | Kim |
| 9,375,517 B2 | 6/2016 | Babcock |
| 9,737,639 B2 | 8/2017 | Babcock |
| 2002/0002353 A1 | 1/2002 | Michal et al. |
| 2003/0165613 A1 | 9/2003 | Chappa et al. |
| 2008/0213334 A1 | 9/2008 | Lockwood et al. |
| 2009/0263449 A1 | 10/2009 | Mcgonigle et al. |
| 2010/0198168 A1 | 8/2010 | Rooijmans |
| 2010/0272774 A1 * | 10/2010 | Chappa .................. A61L 29/085 424/422 |
| 2010/0274012 A1 | 10/2010 | Guire et al. |
| 2011/0046255 A1 | 2/2011 | Rooijmans |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2012/0046384 A2 * | 2/2012 | Kurdyumov .......... A61L 17/145 523/113 |
| 2012/0149934 A1 | 6/2012 | Kurdyumov |
| 2012/0253296 A1 * | 10/2012 | Amano .................. A61L 31/022 604/265 |
| 2013/0143056 A1 | 6/2013 | Swan et al. |
| 2013/0197433 A1 * | 8/2013 | Babcock ............... A61L 29/085 604/103.02 |
| 2013/0337147 A1 | 12/2013 | Chappa et al. |
| 2014/0004158 A1 | 1/2014 | Mcgonigle |
| 2014/0162083 A1 | 6/2014 | Kurdyumov et al. |
| 2014/0193474 A1 | 7/2014 | Babcock et al. |
| 2015/0140107 A1 | 5/2015 | Slager et al. |
| 2016/0271300 A1 | 9/2016 | Babcock |
| 2017/0182224 A1 | 6/2017 | Babcock et al. |
| 2017/0304506 A1 | 10/2017 | Babcock |

FOREIGN PATENT DOCUMENTS

| | | |
|---|---|---|
| EP | 0747071 | 12/1996 |
| EP | 0829264 | 3/1998 |
| EP | 2505215 | 10/2012 |
| EP | 2692365 | 2/2014 |
| JP | 2015503998 | 2/2015 |
| WO | 03055611 | 7/2003 |
| WO | 2006063181 | 6/2006 |
| WO | 2008104573 | 9/2008 |
| WO | 2009091812 | 7/2009 |
| WO | 2011123441 | 10/2011 |
| WO | 2012003293 | 1/2012 |
| WO | 2013109930 | 7/2013 |
| WO | 2015075141 | 5/2015 |
| WO | 2016053831 | 4/2016 |
| WO | 2017116707 | 7/2017 |

OTHER PUBLICATIONS

Allcock, H R. et al., "Molecular Weight," Contemporary Polymer Chemistry, (1990), p. 271.
"Communication Pursuant to Rules 161(1) and 162 EPC," for European Patent Application No. 13704280.0, dated Sep. 3, 2014 (2 pages).
"Communication under Rule 71(3) EPC," for European Patent Application No. 13704280 , dated Aug. 13, 2015 (7 pages).
"International Preliminary Report on Patentability," for PCT/US2013/022202, dated Jul. 31, 2014 (5 pages).
"International Search Report and Written Opinion," from PCT Application No. PCT/US2013/022202, dated Apr. 22, 2013 (9 pages).
Kroschwitz, J I. "Plastics," Concise Encyclopedia of Polymer Science and Engineering, John Wiley and Sons,1990, pp. 462-464.
"Non-Final Office Action," for U.S. Appl. No. 13/745,397 dated Oct. 22, 2015 (21 pages).
"Response to Communication Pursuant to Rules 161(1) and 162 EPC," for EP Patent Application No. 13704280.0, dated Sep. 3, 2014 and filed with the EPO Mar. 10, 2015 (19 pages).
"Extended European Search Report," for European Patent Application No. 15198514.0 dated Mar. 29, 2016 (6 pages).
"Final Office Action," for U.S. Appl. No. 15/165,650 dated Nov. 3, 2016 (18 pages).
"First Office Action," for Chinese Patent Application No. 2013800057179, dated Oct. 9, 2015 (7 pages) with English translation.

(56) References Cited

OTHER PUBLICATIONS

"International Preliminary Report on Patentability," for PCT Application No. PCT/US2015/052565 dated Apr. 13, 2017 (10 pages).
"International Search Report and Written Opinion," for PCT Application No. PCT/US2016/066559 dated Sep. 6, 2017 (10 pages).
"Non-Final Office Action," for U.S. Appl. No. 15/165,650 dated Jul. 11, 2016 (19 pages).
"Office Action," for Japanese Patent Application No. 2014553466 dated Oct. 11, 2016 (5 pages) with English translation.
"Office Action," for Mexican Patent Application No. MX/a/2014/008670 dated Sep. 3, 2017 (1 page), translation only.
"Office Action," for Russian Patent Application No. 2014133462 dated Nov. 17, 2016 (7 pages) with English translation.
"Response to Communication pursuant to Rules 70(2) and 70a(2) EPC," for European Patent Application No. 15198514.0 filed with the EPO Oct. 26, 2016 (2 pages).
"Response to Final Office Action," for U.S. Appl. No. 15/165,650, dated Nov. 3, 2016 and filed Jan. 19, 2017 (5 pages).
"Response to Non-Final Office Action," for U.S. Appl. No. 15/165,650, dated Jul. 11, 2016 and filed Oct. 13, 2016 (7 pages).
"Non-Final Office Action," for U.S. Appl. No. 15/643,564 dated Oct. 16, 2017 (30 pages).
"Office Action," for Japanese Patent Application No. 2017-057269 dated Jan. 9, 2018 (8 pages) with English translation.
"Response to Communication Pursuant to Rules 161(1) and 162 EPC," for European Patent Application No. 15778502.3 filed with the EPO Dec. 6, 2017 (16 pages).
"Response to Non-Final Office Action," for U.S. Appl. No. 15/643,564, dated Oct. 16, 2017 and filed Jan. 30, 2018 (10 pages).

* cited by examiner

LUBRICIOUS MEDICAL DEVICE ELEMENTS

This application claims the benefit of U.S. Provisional Application No. 62/057,063 filed Sep. 29, 2014, the contents of which are herein incorporated by reference.

FIELD OF THE INVENTION

The present invention relates to polymers with lubricious properties. More specifically, the present invention relates to medical device elements formed from polymers with lubricious properties.

BACKGROUND OF THE INVENTION

Medical devices have many applications in the context of modern medicine. Medical devices can include external devices and implantable devices. Devices can be formed of various materials including metals, ceramics, polymers and the like. The usability and/or efficacy of medical devices can be impacted by the functional properties they possess. As such, medical devices can be enhanced through the incorporation of various desirable functional properties.

SUMMARY OF THE INVENTION

Embodiments of the invention include medical device elements formed from polymers with lubricious properties. In an embodiment, a method of forming a medical device element is included. The method can include mixing a first polymeric component and a second polymeric component to form a polymer mixture. The method can further include forming the polymer mixture into the medical device element. The method can also include treating the polymer mixture with at least one of an acid or a base.

In an embodiment, a medical device is included. The medical device can include a lubricious element, the lubricious element comprising a mixture of a first polymeric component and a second polymeric component. The second polymeric component can include a polymer that is treated with at least one of an acid or a base after formation of the element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

Figure 1:
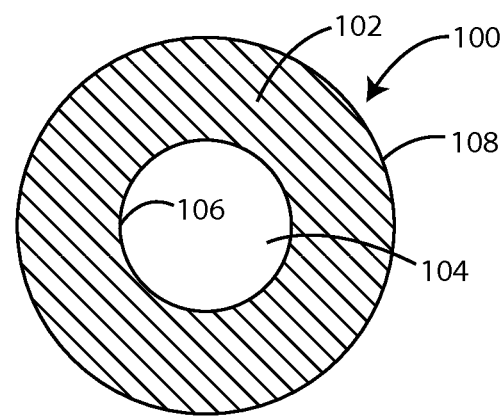
FIG. 1 is a schematic cross-sectional view of a medical device element in accordance with various embodiments herein

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Embodiments herein can include medical devices and/or elements thereof that exhibit desirable functional properties including one or more of lubriciousness and hemocompatibility. In an embodiment, a method of forming a medical device element is included. The method can include mixing a first polymeric component and a second polymeric component to form a polymer mixture. The method can further include forming the polymer mixture into the medical device element. The method can also include treating the polymer mixture with at least one of an acid or a base.

In an embodiment, a medical device is included. The medical device can include a lubricious element, the lubricious element comprising a mixture of a first polymeric component and a second polymeric component. The second polymeric component can include a polymer that is treated with at least one of an acid or a base after formation of the element.

Embodiments herein can be formed from a polymer mixture including a first polymeric component. The first polymeric component can be a single polymer or copolymer or can be a mixture of polymers. In various embodiments, the first polymeric component can include a hydrophobic polymer. In various embodiments, the first polymeric component can include a solvent-soluble hydrophobic polymer.

In some embodiments, the first polymeric component can include a degradable polymer. In some embodiments, the first polymeric component can include a non-degradable polymer.

The first polymeric component can include a polymer selected from the group consisting of polyurethane, polystyrene, polysiloxane, and polyvinyl chloride. In some embodiments, the first polymeric component can include polyurethane.

An exemplary polymer for the first polymeric component can include, but is not limited to, TECOFLEX 85A.

Polymer mixtures used herein to form medical device elements can also include a second polymeric component. In various embodiments, the second polymeric component can include a subunit that undergoes a reaction to yield a carboxylic acid group upon exposure to at least one of an acid or a base. In some embodiments, the second polymeric component can include a subunit that undergoes a ring opening reaction upon exposure to at least one of and acid or a base.

In some embodiments, the second polymeric component can include an acid anhydride group. In some embodiments, the second polymeric component can include a maleic anhydride group. In some embodiments, the second polymeric component can include a methyl vinyl ether and maleic anhydride copolymer. An exemplary polymer for the second polymer component includes, but is not limited to, GANTREZ AN-169.

The second polymeric component can have various molecular weights. In some embodiments, the second polymeric component comprising a polymer having a molecular weight of about 1,000 kD to about 2,500 kD. In some embodiments, the second polymeric component comprising a polymer having a molecular weight of about 1,500 kD to about 2,500 kD. In some embodiments, the second polymeric component comprising a polymer having a molecular weight of about 1,900 kD to about 2,100 kD.

In various embodiments herein, a method of forming a medical device element is included. The method can include mixing a first polymeric component and a second polymeric component to form a polymer mixture. The method can further include forming the polymer mixture into the medical device element. The method can further include treating the polymer mixture with at least one of an acid or a base.

In some embodiments, both polymeric components are dissolved in a suitable solvent before being mixed together. In some embodiments, both polymeric components are dissolved in a suitable solvent after being mixed together. In some embodiments, both polymeric components are mixed together without a solvent.

It will be appreciated that the polymer mixture can be formed into the medical device element in various ways. By way of example, in an embodiment, forming the polymer mixture comprises solvent-casting the polymer mixture. In an embodiment, forming the polymer mixture comprises deposition printing the polymer mixture. In an embodiment, forming the polymer mixture comprises extruding the polymer mixture. In an embodiment, forming the polymer mixture comprises spray coating the polymer mixture. In an embodiment, forming the polymer mixture comprises dip coating the polymer mixture. Various other techniques can also be used.

For purposes of treating the polymer mixture with at least one of an acid or a base, it will be appreciated that various acids or bases can be used. In some embodiments, the compound is a base. In some embodiments sodium bicarbonate is used. The relative amounts of the first polymeric component to the second polymeric component can vary. In some embodiments, the polymer mixture contains from about 1:99 to about 99:1 of the first polymeric component to the second polymeric component by weight. In some embodiments, the polymer mixture contains from about 1:10 to about 10:1 of the first polymeric component to the second polymeric component by weight. In some embodiments, the polymer mixture contains from about 1:2 to about 6:1 of the first polymeric component to the second polymeric component by weight. In some embodiments, the polymer mixture contains from about 1:1 to about 3:1 of the first polymeric component to the second polymeric component by weight.

In some embodiments, the polymer mixture can include a solvent. Various solvents can be used in embodiments herein. In some embodiments, the solvent can be selected from the group consisting of THF, DMF and DMA. In some embodiments, the solvent can specifically include THF.

In various embodiments, other components can also be included. By way of example, in some embodiments, a cross-linking agent, such as a photoactivatable cross-linking agent can also be used. Exemplary photoactivatable cross-linking agents are described in U.S. Publ. Pat. Appl. No. 2012/0046384, the content of which is herein incorporated by reference.

Medical device elements herein can take on many different forms. In some embodiments, the medical device element can be a substrate. In some embodiments, the medical device element can be a tube. In some embodiments, the medical device element can be a shaft of a medical device, including but not limited to, a catheter shaft. In some embodiments, the medical device element can be a coating.

Referring now to FIG. 1, a cross-sectional view of a medical device element 100 is shown in accordance with embodiments herein. In this embodiment, the medical device element 100 includes a wall member 102 defining a lumen 104. The wall member 102 can be formed from the polymer mixture including the first polymeric component and the second polymeric component. The wall member 102 includes a luminal surface 106 and an abluminal surface 108. The luminal surface 106 and/or the abluminal surface 108 can exhibit desirable properties including, but not limited to, one or more of lubriciousness and hemocompatibility.

Figure 2:
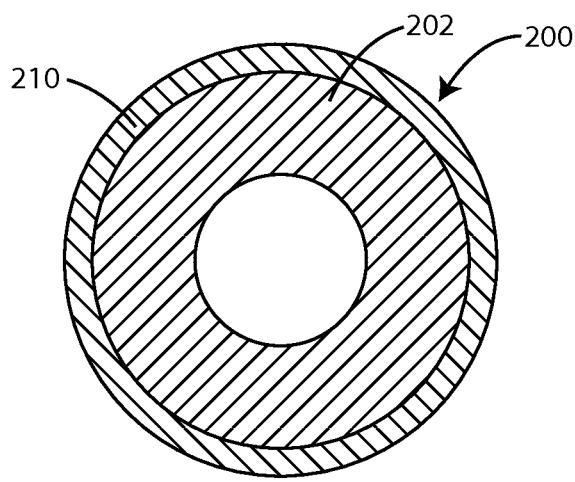
FIG. 2 is a schematic cross-section view of a medical device element in accordance with various embodiments herein.

Referring now to FIG. 2, a cross-sectional view of a medical device element 200 is shown in accordance with embodiments herein. In this embodiment, the medical device element is a coating. Specifically, the medical device element 200 is a coating 210 disposed over a wall member 202.

The present invention may be better understood with reference to the following examples. These examples are intended to be representative of specific embodiments of the invention, and are not intended as limiting the scope of the invention.

EXAMPLES

Example 1

Formation and Assessment of Tubing 15 mg of a photoactivatable cross-linking agent (as described in U.S. Publ. Pat. Appl. No. 2012/0046384, the content of which is herein incorporated by reference) was dissolved into a few drops of THF and one drop of water. 10 ml of a solution of TECOFLEX 85A polyurethane (100 mg/ml in THF) was added to the cross-linking agent solution. 5 ml of a solution of GANTREZ, AN-169 (methyl vinyl ether and maleic anhydride copolymer) (100 mg/ml in THF) was then added to the solution.

The solution was coated onto a section of TEFLON tubing in multiple coats followed by the application of ultraviolet radiation after each coat. The materials were then dried overnight and the inner TEFLON tubing was removed leaving behind a tube of experimental material. The experimental material was then soaked in a solution of 0.1M sodium bicarbonate for 30 minutes, blown out and air dried overnight.

Functional properties of the experimental material were assessed through a pinch test (lubricity) and a blood loop assay (hemocompatibility). The lubricity was found to be better than comparable polyurethane tubing. The experimental material also exhibited greater hemocompatibility (lower thrombus score and lower thrombus weight) than comparable polyurethane tubing.

It should be noted that, as used in this specification and the appended claims, the singular forms "a," "an," and "the"

include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. A method of forming a medical device comprising:
    mixing a first polymeric component comprising a polyurethane, a second polymeric component comprising a methyl vinyl ether and maleic anhydride copolymer, and a photoactivatable cross-linking agent to form a polymer mixture;
    forming the polymer mixture into a substrate of the medical device by applying the polymer mixture onto a form or mold and then removing the form or mold from the polymer mixture; and
    treating a surface of the polymer mixture with at least one of an acid or a base.

2. The method of claim 1, the first polymeric component further comprising a polymer selected from the group consisting of, polystyrene, polysiloxane, and polyvinyl chloride.

3. The method of claim 1, the second polymeric component comprising a subunit that undergoes a reaction to yield a carboxylic acid group upon exposure to at least one of an acid or a base.

4. The method of claim 1, the second polymeric component comprising a subunit that undergoes a ring opening reaction upon exposure to at least one of an acid or a base.

5. The method of claim 1, the second polymeric component comprising a polymer having a molecular weight of about 1,900 kD to about 2,100 kD.

6. The method of claim 1, wherein the polymer mixture contains from about 1:1 to about 3:1 of the first polymeric component to the second polymeric component by weight.

7. The method of claim 1, wherein forming the polymer mixture into a substrate of the medical device comprises forming the polymer mixture into a hollow tube.

8. The method of claim 1, wherein forming the polymer mixture into the substrate of the medical device by applying the polymer mixture onto a form or mold comprises applying the polymer mixture onto tubing and then removing the tubing from the polymer mixture.

* * * * *